United States Patent
't Hooft et al.

(10) Patent No.: US 6,733,814 B2
(45) Date of Patent: May 11, 2004

(54) FOOD COMPOSITION SUITABLE FOR SHALLOW FRYING COMPRISING SUNFLOWER LECITHIN

(75) Inventors: Cor 't Hooft, Maarssen (NL); Marcelle Kommer van den, Vlaardingen (NL); Jacobus Cornelis Segers, Vlaardingen (NL)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 260 days.

(21) Appl. No.: 10/025,296

(22) Filed: Dec. 19, 2001

(65) Prior Publication Data

US 2002/0122867 A1 Sep. 5, 2002

(30) Foreign Application Priority Data

Dec. 21, 2000 (EP) .............................. 00204763

(51) Int. Cl.$^7$ .............................. A23D 9/007
(52) U.S. Cl. .................. 426/604; 426/662; 554/80; 554/83
(58) Field of Search ............... 426/604, 662; 554/80–83

(56) References Cited

U.S. PATENT DOCUMENTS

| | | | |
|---|---|---|---|
| 3,505,074 A | * | 4/1970 | Pardun ................ 554/80 |
| 4,584,141 A | * | 4/1986 | Paulitz et al. ........... 554/190 |
| 4,608,267 A | * | 8/1986 | Dutilh ................. 426/662 |
| 4,874,553 A | * | 10/1989 | Hager, Jorg et al. ....... 554/80 |
| 5,214,171 A | * | 5/1993 | Dijkstra et al. .......... 554/83 |

FOREIGN PATENT DOCUMENTS

| | | |
|---|---|---|
| DE | 297 08 250 | 5/1997 |
| EP | 0 265 003 | 10/1987 |
| EP | 0 253 429 | 1/1988 |
| FR | 2 766 737 | 7/1997 |
| GB | 1113241 | * 5/1968 |
| GB | 1215868 | * 7/1968 |
| GB | 1355967 | * 9/1970 |

OTHER PUBLICATIONS

Smiles, A. 1988. JAOCS 65(7)1151–1155..*
Smiles, A. 1989, JAOCS 66(3)348–352.*
Lambourne, D. 1999. JAOCS 76(1)67–72.*
European Search Report.
Paraskevov, Journal of Milk & Dairy Products, vol. 43, No. 3, 1994; "Cholesterol free dairy products"; Abstract XP–002166913.
Hollo, J. et al., "Sunflower Lecithin and Possibilities for Utilization", JAOCS Journal of the American Oil Chemists Society, vol. 70, No. 10, Oct. 1, 1993, pp. 997–1001.
D.R. McCaskill et al., "Lecithin As A Food Ingredient—Properties And Functions", Food Tech Europe, Sept/Oct. 1996, pp. 146 and 148.
Zmarlicki et al., Journal of Milk & Dairy Products, vol. 53, No. 11, 1999; "The use of anhydrous milk fat in production of protein–free dairy spreads"; Abstract XP–002166914.

* cited by examiner

*Primary Examiner*—Carolyn Paden
(74) *Attorney, Agent, or Firm*—Milton L. Honig

(57) ABSTRACT

The invention concerns a food composition, suitable for shallow frying, comprising triglycerides, wherein least 60 wt. % of triglycerides is of vegetable origin, and 0.05–3 wt. % sunflower lecithin. The invention further concerns a process for the preparation of hydrolyzed sunflower lecithin.

4 Claims, No Drawings

FOOD COMPOSITION SUITABLE FOR SHALLOW FRYING COMPRISING SUNFLOWER LECITHIN

FIELD OF THE INVENTION

The invention relates to food compositions suitable for shallow frying. The invention further relates to a process for hydrolysis of native lecithin, resulting in a product suitable for addition to food compositions suitable for shallow frying.

BACKGROUND OF THE INVENTION

Food compositions suitable for shallow frying are well known. Examples of such food compositions are butter, margarine, including liquid margarine, spreads, such as low fat spread and cooking milk. The food compositions are often multifunctional, i.e. they can be used for different purposes, e.g. baking and spreading on bread, next to suitability in frying.

When used in shallow frying, the spattering performance of the food compositions is important. Spattering during shallow frying should be avoided as much as possible.

Lecithin is well known to have an anti-spattering effect. The improvement of spattering performance is therefore an important reason for incorporation of lecithin in food compositions Lecithin is a widely used term for a complex mixture of phosphatides produced from a variety of vegetable and animal sources. Examples of the phosphatides are phosphatidyl choline (PC), phosphatidyl ethanolamine (PE), phosphatidyl inositol (PI), phosphatidic acid (PA) and acetylated phosphatidyl ethanolamine (aPE). Hydrolyzed phosphatides are designated by the prefix lyso-, for instance lyso-PC or LPC.

Vegetable lecithins are derived from crude vegetable oils or fats, in which the lecithins are present as a colloidal solution. They are usually removed in a degumming step in which lecithin is precipitated, e.g. by injection of steam into the oil or fat or by injection of water or an aqueous solution.

The lecithins are available in the market as a very viscous substance containing 60–65 wt. % phosphatides, 30–35 wt. % oil and about 5–10% of other compounds, e.g. sterol. Such mixture is herein referred to as native lecithin.

Lecithins are usually designated depending on their origin (e.g. soybean lecithin, sunflower lecithin, rapeseed lecithin, canola lecithin, cotton seed lecithin, egg lecithin, etc).

By far the most important native lecithin is soybean lecithin, which is derived from soya bean oil. Next to native soybean lecithin, also de-oiled soybean lecithin (from which the oil fraction has been removed) and hydrolyzed soybean lecithin are known and commercially available.

Due to the large predominance of soybean lecithin relative to the other lecithins, the skilled person generally uses the expression lecithin when actually soybean lecithin is meant.

The use of lecithin as anti-spattering agent in a food composition is for instance illustrated in EP-B-265 003, which discloses a food composition with reduced fat content, wherein the fat phase has up to 75 wt. % fat. The emulsion comprises an emulsifier system with a mixture of phospholipids containing phosphatidyl choline and phosphatidyl ethanolamine in a ratio exceeding 3:1. The lecithin emulsifier system is prepared by extracting soybean lecithin with a polar extraction solvent, for instance an alcohol.

According to U.S. Pat. No. 3,505,074 the emulsifying properties of phosphatides, for example as anti-spattering agent in margarine are improved by partial hydrolysis of the phosphatides.

EP-B-253 429 discloses a surface-active composition, which comprises at least 3% lysophosphatidylethanolamine and wherein the hydrolysis ratio of the degree of hydrolysis of phosphatidylethanolamine and the degree of hydrolysis of phosphatidylcholine is higher than 1.5. The surface-active composition, which is reported to give improved spattering performance, is prepared in a process, which involves fractionation and subsequent hydrolysis.

Although the phosphatide compositions prepared according to the above prior art show good spattering performance, they have the disadvantage that they involve in their preparation additional process steps like fractionation and hydrolysis. A process step involving hydrolysis further has the potential disadvantage to increase the level of foaming of food compositions comprising the hydrolyzed lecithin. Therefore the use of native soybean lecithin is still very common in frying compositions.

We have found that although the spattering performance of native soybean lecithin may be sufficient in food compositions comprising 80 wt. % of a fatty phase, it is insufficient when food composition are prepared having a lower fat content, e.g. 70 wt. % fat, 60 wt. % fat or below.

J. Hollo et al., JAOCS, Vol. 70, no. 10 (1993), 997–1001 discusses the fractionation, acylation and enzymatic hydrolysis of sunflower lecithin and its possibilities for utilization. The hydrolysis time reported is 1 to 5 hours. No description of use of sunflower lecithin in food compositions is given.

S. Zmarlicki, Prezemysl-Spozywczy,53 (11), 63–65 describes that a series of 23 protein-free dairy spreads were produced having 0.4% sunflower lecithin as emulsifier. The spreads were produced using 40–80% anhydrous milk-fat, 0–30% sunflower oil (0–42.8% in the fat phase) and 0.02–0.04% commercial butter flavouring, and had good taste and flavour properties. The spreads have a high animal fat content and the spattering performance in shallow frying is not mentioned.

SUMMARY OF THE INVENTION

An object for the invention is to improve the spattering performance of the prior art food compositions, when used in shallow frying.

A further object of the invention is to provide a food composition that has improved properties related to both spattering performance and foaming.

Another object of the invention is to provide a food composition having health benefits, for instance a lowering effect on the level of blood cholesterol in humans.

Yet another object of the invention is to provide a food composition that can be prepared from naturally occurring ingredients with less process steps involved.

One or more of these objects are attained according to the invention providing a food composition, comprising triglycerides, wherein at least 70 wt. % of the triglycerides is of vegetable origin, and 0.05–3 wt. % sunflower lecithin.

One or more of the objects is further attained by a food composition, suitable for shallow frying comprising 0.05–3 wt. % sunflower lecithin, wherein the sunflower lecithin is hydrolyzed or fractionated.

Hydrolyzed sunflower lecithin is herein understood to be sunflower lecithin, wherein the degree of hydrolysation as defined in the examples is 0.05 or higher.

The invention further provides an improved process for the hydrolysis of lecithin, in which the hydrolysis time is reduced, wherein sunflower oil is subjected to a degumming operation to give native sunflower lecithin, wherein the native sunflower lecithin is subjected to hydrolysis, characterized in that the difference in acid value between the hydrolysis product and the native sunflower lecithin ($\Delta AV$) is 2–15.

DETAILED DESCRIPTION OF THE INVENTION

The following definitions will be used throughout the description and claims. Where ranges are mentioned, the expression from a to b is meant to indicate from and including a, up to and including b, unless indicated otherwise. The term's 'oil' and 'fat' are used interchangeably.

The following abbreviations of phospholipids are used herein: PC (Phosphatidyl choline), PI (Phosphatidyl Inositol), PE (Phosphatidyl ethanolamine) aPE (acetylated phosphatidyl ethanolamine) and PA (Phosphatidic acid), the hydrolysed forms of these phospholipids being indicated with the suffix L (for instance LPC for lyso-phosphatidyl choline).

The food compositions according to the invention may be water-in-oil emulsions, for instance spreads or margarines, oil-in-water emulsions suitable for shallow frying, such as for instance water-continuous shallow frying media or may substantially consist of fat or oil.

The amounts of the oil and water phase in the product are not critical. For instance the food composition may comprise 30–100 wt. % fat phase and 0–70 wt. % aqueous phase. Preferably the food composition comprises 40–100 wt. % fat phase and 0–60 wt. % aqueous phase. More preferably the food composition is a water in oil emulsion comprising 60–90 wt. % fat phase and 10–40 wt. % aqueous phase.

A fat phase content of around 80 wt.% is common for margarines, as well as around 70 or 60%. The invention also relates to products that contain nearly 100% fat phase: Though in these food compositions primary spattering as hereunder defined may not be important, secondary spattering is improved.

The food composition according to the invention may be a liquid margarine. A liquid margarine is herein defined as a pourable water-in-oil emulsion comprising generally from 1–40, preferably 5 to 30 wt. % water, based on total composition weight.

The fat phase may comprise any triglyceride oil, as long as at least 70 wt. % of triglycerides is of vegetable origin. A fat phase rich in triglycerides comprising (poly)unsaturated fatty acid residues is highly preferred. Therefore the fat is preferably selected from the group comprising sunflower oil, soybean oil, rapeseed oil, cottonseed oil, olive oil, corn oil, groundnut oil, maize oil, Linola oil, linseed oil, coconut oil, palmkernel oil and/or combinations thereof. These fats may be partially hydrogenated. The fat phase may comprise sucrose polyesters which are used as fat replacers, or may contain functional ingredients, such as sterols or stanols, or esters thereof.

An amount of fat of animal origin, for instance butter fat may be advantageous, e.g. for taste, however, the total of these fats should be below 30 wt. % of total triglycerides in the food composition.

Optionally the food composition comprises in addition to these fats a hard fat component selected from the group comprising: hardened rapeseed oil, hardened soybean oil, hardened rapeseed oil, hardened cottonseed oil, hardened corn oil, hardened groundnut oil, palmoil, hardened palmoil, palmoil fractions, hardened palmoil fractions, butterfat or butterfat fractions. These fats are optionally partly or fully hydrogenated and/or interesterified to obtain the desired structuring properties. This hard fat may partly serve to impart structure and/or stability to the products.

The fat phase may comprise ingredients which are common in frying products, such as colorant, e.g. carotene, fat soluble flavours and vitamins, mono- and/or diglycerides, etc.

The optional aqueous phase of the food composition may comprise ingredients which are common in frying products, such as proteins, flavours which are water soluble, emulsifiers, thickeners, salt, dairy ingredients, preservatives etc.

The food compositions according to the invention may be packaged in usual manner. Margarines may be packed in a wrapper, tub or in a bottle. Other food products may be packed in bottles, tins, foil, paper, etc. or sold as such.

The sunflower lecithin may be hydrolyzed or fractionated. Hydrolysis may be executed in a known manner, e.g. in an enzymatic process with phospholipase. However the reaction time may be shorter than a reaction time usual for soybean lecithin.

Preferably the sunflower lecithin is hydrolyzed and the degree of hydrolysis of the sunflower lecithin is 0.1 to 0.5, more preferably 0.2 to 0.4, even more preferably 0.25–0.33. The degree of hydrolysis is herein defined as the ratio between wt % lyso-PE and wt % (lyso-PE+PE).

The invention further relates to a process for the preparation of hydrolyzed sunflower lecithin, wherein sunflower oil is subjected to a degumming operation to give native sunflower lecithin, wherein the native sunflower lecithin is then subjected to hydrolysis.

Preferably the reaction time during hydrolysis is such that the difference in acid value between the hydrolysis product and the native sunflower lecithin ($\Delta AV$) is 2–15, more preferable 5–12, even more preferably 7–9. The measurement of acid value is described herein in the experiments.

Under these conditions an improved spattering performance of food products with the hydrolysed sunflower lecithin is obtained.

Preferably the hydrolysis process is conducted using an enzymatic process using phospholipase A-2 enzyme.

The sunflower lecithin may also be fractionated, e.g. by extraction with an alcohol, for instance ethanol.

Food products according to the invention show reduced spattering upon preferred use as shallow frying product. Shallow frying products are defined as products used for shallow frying, i.e. frying wherein the food product to be fried is fried in a thin layer of frying product, i.e. the product is not completely immersed in the frying product. An example of shallow frying is frying of meat, fish or vegetables in a pan. On the contrary, in deep frying, the food product to be fried is usually completely immersed in the frying product. An example of deep frying is the frying of potato chips in a deep oil-filled frying pan.

During shallow frying with a frying product comprising an aqueous phase, such as margarine, generally spattering will occur in two instances, separated in time. A first type of spattering, generally referred to as primary spattering, may occur when the margarine is heated in the frying pan. Primary spattering is a result of explosion-like evaporation of superheated water droplets, originating from the aqueous phase of the margarine. A second type of spattering occurs, when water, or a food product that releases water, such as meat, fish or vegetable is introduced into the heated frying product. This type of spattering, again due to explosive evaporation of superheated water, is called secondary spattering.

Values for primary spattering (SV1) and secondary spattering (SV2) are herein determined according to the method illustrated in the examples.

The invention is now illustrated by the following, non-limiting examples

EXAMPLES

Determination of Spattering Value in a Spattering Test

Primary spattering (SV1) was assessed under standardised conditions in which an aliquot of a food product was heated in a glass dish and the amount of fat spattered onto a sheet of paper held above the dish was assessed after the water content of the food product had been evaporated by heating.

Secondary spattering (SV2) was assessed under standardised conditions in which the amount of fat spattered onto a sheet of paper held above the dish is assessed after injection of a quantity of 10 ml water into the dish.

In assessment of both primary and secondary spattering value, an amount of food product containing 20 g fat (e.g. 25 g of a 80% fat spread) was heated in a 15 cm diameter glass dish on an electric plate thermostated at about 205° C. The fat that spattered out of the pan by force of expanding evaporating water droplets was caught on a sheet of paper situated at 25 cm above the pan (SV1 test). Subsequently a quantity of 10 ml water was injected into the dish and again the fat that spattered out of the pan by force of expanding evaporating water droplets was caught on a sheet of paper situated above the pan (SV2 test).

The images obtained were compared with a set of standard pictures numbered 0–10 whereby the number of the best resembling picture was recorded as the spattering value. 10 indicates no spattering and zero indicates very bad spattering. The general indication is as follows.

| Score | Comments |
|-------|----------|
| 10 | Excellent |
| 8 | Good |
| 6 | Passable |
| 4 | Unsatisfactory for SV1, almost passable for SV2 |
| 2 | Very poor |

Typical results for household margarines (80 wt. % fat) are 8.5 for primary spattering (SV1) and 4.6 for secondary spattering (SV2) under the conditions of the above mentioned test.

Determination of Acid Value and ΔAV (Delta Acid Value)

Acid values are measured at-line to monitor the hydrolysis profile. The method, based on the AOCS standard method JA 6-55(97), involves dissolving a weighed phospholipd sample (approximately 0.5 grams) in petroleum ether (60 ml) followed by addition of 60 ml of neutralized ethanol. The dispersion created was continuously mixed and titrated against a 0.1 M NaOH solution and the endpoint is detected with phenolphtalein. All acid values were expressed as mg KOH/g phospholipid equivalents.

ΔAV (Delta acid value) is the difference in acid value between the hydrolysed phospholipid sample and the acid value of the native sunflower lecithin which is the starting product for the hydrolysis (expressed in mg KOH/g phospholipid equivalents).

Determination of Phosphatide Amounts

Phosphatide wt % amounts herein are determined by 31P-NMR (nuclear magnetic resonance) analysis. The method is described in Glonek, T, and T. E. Merchant, 31P NMR Phospholipid Profiling, in *Advances in Lipid Methodology*, edited bt W. W. Christie, The Oily Press, Ltd. West Ferry, 1995, Vol. 3, pp. 35–37.

Example 1

Hydrolysis of Sunflower Lecithin

In a 1 liter stainless steel vessel, equipped with an Ultra turrax stirrer and placed in a waterbath (Lauda), heated at 50 degrees C., 420 g sunflower lecithin in 272 g demineralized water was prepared. The mixture was stirred until a water-continuous mixture was obtained and then the pH was adjusted to 7.0 with 25% ammonia solution.

Native sunflower lecithin was obtained from Cereol Novenyollajipari RT, Budapest, Hungary. This native sunflower lecithin had an acetone insoluble fraction of 56.5 wt. %.

To the mixture 42 ml demineralized water and 0.035 ml enzyme solution Lecitase (Novo Nordisk Co., Denmark) were added. The resulting sludge was heated to 50 degrees C. and stirred at 70 rpm.

The hydrolysis of lecithin was followed by taking samples from the sludge, drying to a water content lower than 1.5 wt. %, and measuring the degree of hydrolysis. The results are given in table 1.

TABLE 1

Results of hydrolysis of sunflower lecithin

| Reaction time (min.) | 0 | 30 | 60 | 90 | 120 |
|---|---|---|---|---|---|
| Degree of hydrolysis | 0.08 | 0.26 | 0.33 | 0.47 | 0.46 |
| Acid Value (mgKOH/g) | 34.8 | 39.9 | 41.7 | 42.9 | 45 |
| ΔAV | | 5.1 | 6.9 | 8.1 | 10.2 |
| Phospholipid composition (% w/w) | | | | | |
| PC | 14.2 | 11.3 | 10.9 | 10.3 | 9.5 |
| PI | 8.6 | 7.5 | 7.6 | 8.4 | 8.1 |
| PE | 4.9 | 2.6 | 2.9 | 1.8 | 2.2 |
| PA | — | — | — | — | — |
| LPC | 0.9 | 2.9 | 3.6 | 3.7 | 3.4 |
| LPI | 0.5 | 0.7 | 1.9 | 1.1 | 1.2 |
| LPE | 0.4 | 0.9 | 1.4 | 1.6 | 1.9 |
| LPA | — | — | — | — | — |
| aPE | 0.5 | 0.2 | — | — | — |
| SV 1 | 8 | 7.75 | 8 | 7.75 | 7.75 |
| SV 2 | 7 | 6.75 | 7.5 | 7 | 7 |

SV1 and SV2 were determined in a food composition prepared according to example 2.

Example 1 shows that an optimum spattering performance for sunflower lecithin is reached at a hydrolysis time of 60 minutes. This is a very short hydrolysis time compared to the hydrolysis of soybean lecithin, where hydrolysis times of 10–12 hours are needed under conditions of example 1.

Example 2

Preparation Food Composition

A food composition with the following composition was prepared:

Fat phase (80 wt. % of composition): 79.48 wt. % fat blend (fats solids profile: $N_{10}=35$, $N_{20}=20.0$, $N_{30}=8.5$ and $N_{40}=0$), 0.48 wt. % lecithin, 0.04 wt. % saturated monoglyceride (Hymono 8903); water phase (20 wt. % of composition): 0.96 wt. % salt, 1.06 wt. % sour whey powder and 17.98 wt. % tap water. The pH of the water phase was adjusted at 4.6 with 10 wt. % citric acid.

A pre-mix of the ingredients was passed through a Votator line with 3 scraped surface heat exchangers (A-units) one stirred crystallizer (C-unit) and a resting tube (B-unit) in a A-C-A-A-B sequence, the A units and C unit were operated at 500 rpm. The food composition leaving the B-unit had a temperature of 11 degrees C. and was packed in wrappers.

The lecithins designated as Bolec were obtained from Unimills, Zwijndrecht, Netherlands and having an acetone insoluble fraction of 62 wt. % (a measure indicative of total phospholipid content).

Native sunflower lecithin was obtained from Cereol Novenyollajipari RT, Magyargorszag, Budapest, Hungary, having an acetone insoluble fraction of 56.5 wt. %.

Hydrolyzed sunflower lecithin was obtained according to the procedure in example 1, with a reaction time of 60 minutes.

Solids profiles (N-values) of the fat blend may be determined by means of NMR, using the method described in "Fette, Seifen, Anstrichmittel" 80, (1978), 180–186.

The results of the spattering performance test are given in table 2.

TABLE 2

Spattering performance for 80 wt. % fat food composition

| Spattering perf. | Native soybean lecitin (Bolec ZT) | Native sunflower lecithin | Hydrolyzed soybean lecithin (Bolec MT) | Hydrolyzed sunflower lecithin |
|---|---|---|---|---|
| SV1 | 8.75 | 8.0 | 8.0 | 8.0 |
| SV2 | 5.5 | 7.0 | 7.25 | 7.5 |

Table 2 shows that the spattering performance SV 2 is improved. The spattering performance SV1 for native lecithins was comparable taking into account that the total phospholipid content of the soybean lecithin was about 10% higher (acetone insoluble fraction 62 instead of 56.5%).

Example 3

Preparation of a Food Composition

Example 2 was repeated, however with the following composition:

69.95 wt. % fat blend (same as in example 2), 0.4 wt. % lecithin, 0.05 wt. % saturated monoglyceride (Hymono 8903), 29.0 wt. % water, 0.7 wt. % salt, 0.3 wt. % sour whey powder; pH 4.6

The results of the spattering performance test are given in table 3.

TABLE 3

Spattering performance for 70 wt. % fat food composition

| Spattering perf. | Native soybean lecitin (Bolec ZT) | Native sunflower lecithin | Hydrolyzed soybean lecithin (Bolec MT) | Hydrolyzed sunflower lecithin |
|---|---|---|---|---|
| SV1 | 7.25 | 7.0 | 7.0 | 7.0 |
| SV2 | 6.0 | 6.75 | 6.25 | 7.5 |

Table 3 shows that the spattering performance SV2 is improved. The spattering performance SV1 for native lecithins was comparable taking into account that the total phospholipid content of the soybean lecithin was about 10% higher (acetone insoluble fraction 62 instead of 56.5%).

What is claimed is:

1. Process for the preparation of hydrolyzed sunflower lecithin, comprising degumming sunflower oil to give native sunflower lecithin, and then hydrolyzing the native sunflower lecithin, characterized that the difference in acid value between the hydrolysis product and the native sunflower lecithin ($\Delta AV$) is 2–15.

2. Process according to claim 1, wherein the difference in acid value between the hydrolysis product and the native sunflower lecithin ($\Delta AV$) is 5–12.

3. Process according to claim 1, wherein the difference in acid value between the hydrolysis product and the native sunflower lecithin ($\Delta AV$) is 7–9.

4. Process according to claim 1, wherein the hydrolysis is conducted using an enzymatic process using phospholipase A-2 enzyme.

* * * * *